(12) United States Patent
Heikkilä et al.

(10) Patent No.: US 6,428,476 B1
(45) Date of Patent: Aug. 6, 2002

(54) METHOD OF CONFIRMING PERFORMER OF EXERCISE

(75) Inventors: Ilkka Heikkilä; Seppo Nissilä; Raimo Siurua, all of Oulu (FI)

(73) Assignee: Polar Electro Oy, Kempele (FI)

( * ) Notice: Subject to any disclaimer, the term of this patent is extended or adjusted under 35 U.S.C. 154(b) by 24 days.

(21) Appl. No.: 09/686,510

(22) Filed: Oct. 11, 2000

(30) Foreign Application Priority Data

Oct. 13, 1999 (FI) .............................................. 19992206

(51) Int. Cl.$^7$ ................................................ A61B 5/00
(52) U.S. Cl. ........................................ 600/300; 600/508
(58) Field of Search ................................ 600/300, 301, 600/508, 520, 503; 482/8, 900

(56) References Cited

U.S. PATENT DOCUMENTS

| | | | |
|---|---|---|---|
| 5,438,983 A | * | 8/1995 | Falcone ........................ 600/301 |
| 5,615,685 A | * | 4/1997 | Suga ............................ 60/300 |
| 5,706,822 A | | 1/1998 | Khavari |
| 6,104,947 A | * | 8/2000 | Heikkilä et al. ............. 600/519 |
| 6,277,080 B1 | * | 8/2001 | Nissilä et al. ................ 600/508 |

FOREIGN PATENT DOCUMENTS

| | | |
|---|---|---|
| EP | 0199442 | 10/1986 |
| EP | 0516898 A1 | 12/1992 |
| EP | 0 0733340 A1 | 10/1996 |
| EP | 0922434 A1 | 6/1999 |
| JP | 10192260 | 7/1998 |

OTHER PUBLICATIONS

European Search Report dated Feb. 7, 2001.
Finnish Patent Office, Search Report, Mar. 13, 2001.
European Patent Office, Search Report, Aug. 27, 2001.

* cited by examiner

*Primary Examiner*—Robert L. Nasser
*Assistant Examiner*—Patricia Mallari
(74) *Attorney, Agent, or Firm*—Hoffmann & Baron, LLP (57) ABSTRACT

The invention presents a system for confirming a performer of a fitness exercise. The system includes a heart rate monitor (104) for measuring heart rate parameters (404A to 404N) associated with the fitness exercise from the heart rate of the performer. The system also includes a mathematical model (406) including dependence information between heart rate parameters (404A to 404N) and classes classifying the performer in classes (402A to 402N) such as age or weight. Heart rate parameter data measured from the performer and information in the mathematical model are utilized in identifying the performer of the fitness exercise.

31 Claims, 6 Drawing Sheets

METHOD OF CONFIRMING PERFORMER OF EXERCISE

BACKGROUND OF THE INVENTION

1. Field of the Invention

The invention relates to a method, arrangement, heart rate monitor, computer software product and computer for identifying a performer of an exercise.

2. Brief Description of the Related Art

In health care, it is often necessary for a doctor in a patient-doctor relationship to be sure that the patient has followed the instructions for rehabilitation given by the doctor. It is important to follow the instructions so as to enable the strenuousness of the rehabilitation to be adjusted to conform with the way in which the patient's condition progresses. This is also the case in sports as regards the situation between a coach and a trainee wherein the coach, who cannot always be present when the trainee performs the exercises, cannot be sure that the trainee has performed all exercises assigned by the coach. In such a case, the coach may draw false conclusions about how the training affects the way in which the trainee advances, which may further lead to false conclusions when future training programs are being planned.

An example of a rehabilitation or training instruction would be a situation wherein a person being instructed, such as a patient, is given an exercise program by an instructor, such as a fitness instructor, company nurse or company doctor. The program includes exercise three times a week during the next month. During the exercise period, the patient writes down in an exercise diary or informs the instructor orally how he or she carries out the exercise program. Alternatively, the patient may also utilize a heart rate monitor during the exercise and store a recorded heart rate every time he or she exercises or store the mean heart rate during the exercise or other heart rate parameters describing the exercise in the memory of the heart rate monitor. The essential point is that on the basis of the stored information, it can in one way or another be ascertained that the exercise program has been followed according to the instructions.

A problem of the current methods is that the authenticity of the exercise diaries and stored heart rate recordings cannot be verified. The instructor cannot be sure that it is really the person being instructed that has performed the exercises listed in the training program. Of course, for example, a code to identify the person being instructed can be arranged in the heart rate monitor, but it still cannot be verified whether the particular person has performed the exercise. In addition to the problem of confirming the user, another problem is, for example, that the same heart rate information stored in the heart rate monitor can be used several times by copying the information as if it were associated with a new exercise.

SUMMARY

An object of the invention is to provide an improved method of confirming a performer of a fitness exercise so that the aforementioned problems can be alleviated. This is achieved by a method to be disclosed, hereinafter, which is a method of confirming a performer of a fitness exercise, the method comprising measuring heart rate information associated with the performer of the fitness exercise as regards the fitness exercise; forming an identifier value in one or more classes on the basis of one or more parameters of the measured heart rate information by means of a mathematical model comprising dependence information between said parameter of the heart rate information and said class; confirming the performer of the fitness exercise by comparing in said one or more classes the identifier value with a reference value formed for the performer of the fitness exercise in the class.

The invention further relates to an arrangement for confirming a performer of a fitness exercise, the arrangement comprising a heart rate monitor for measuring one or more parameters of heart rate information associated with the performer of the fitness exercise as regards the fitness exercise; identifier equipment comprising means for classifying the performer of the fitness exercise in one or more classes; a mathematical model comprising dependence information between said one or more parameters of the heart rate information and said one or more classes; the identifier equipment further comprising calculating means for forming a reference value in one or more classes on the basis of one or more parameters of the heart rate information by means of the mathematical model; means for comparing in said one or more classes the identifier value of the performer of the fitness exercise with the reference value formed for the performer of the fitness exercise in the class; means for concluding the performer of the fitness exercise on the basis of the comparison between the identifier values and the reference values.

The invention also relates to a heart rate monitor comprising means for measuring one or more parameters of heart rate information associated with a performer of a fitness exercise as regards the fitness exercise. The heart rate monitor comprises means for forming an execution date of the fitness exercise in connection with the fitness exercise and for adding said date to the heart rate information collected on the fitness exercise in order to confirm the execution date of the fitness exercise.

The invention also relates to a computer software product for confirming a performer of a fitness exercise, the product comprising a program stored in a device for storing programs and readable by a computer. The computer software product comprises the following method steps: receiving heart rate information associated with the performer of the fitness exercise as regards the fitness exercise; forming an identifier value on the basis of parameters of the measured heart rate information in one or more classes by means of a mathematical model comprising dependence information between the parameters of the heart rate information and the classes; confirming the performer of the fitness exercise by. comparing in said one or more classes the identifier value with a reference value formed for the performer of the fitness exercise in the class.

The invention also relates to a computer for confirming a performer of a fitness exercise, the computer comprising means for receiving one or more parameters of heart rate information associated with the performer of the fitness exercise as regards the fitness exercise; means for classifying the performer of the fitness exercise in one or more classes; a mathematical model comprising dependence information between said one or more parameters of the heart rate information and said one or more classes; calculating means for forming a reference value in one or more classes on the basis of one or more parameters of the heart rate information by means of the mathematical model; means for comparing in said one or more classes the identifier value of the performer. of the fitness exercise with a reference value formed for the performer of the fitness exercise in the class; means for concluding the performer of the fitness exercise on the basis of the comparison between the identifier values and the reference values.

Preferred embodiments of the invention are disclosed in the dependent claims.

In a solution of the invention, in order to confirm a performer of a fitness exercise a person whose execution of an exercise is to be monitored preferably uses a heart rate monitor. The heart rate monitor is a device used in sports and medicine to measure a human heart rate either from an electric impulse transmitted by the heart or from the pressure caused by the heart rate in blood vessels. A known structure of the heart rate monitors is, for example, such that an electrode belt is arranged around a user's chest to measure the heart rate by two electrodes. The electrode belt inductively transmits the measured heart rate information to a receiver unit worn on the wrist. The receiver unit often also comprises a display for showing the heart rate, and a user interface to enable other functions of the heart rate monitor to be used. In the situation described above, the heart rate monitor refers to an integrated whole comprising the electrode belt and the receiver. The heart rate monitor may also consist of one piece only such that the display means are also located on the chest, in which case no information needs to be transmitted to a separate receiver unit. Furthermore, the heart rate monitor may have such a structure that it only comprises a device arranged on the wrist, which operates without an electrode belt arranged on the chest, measuring the heart rate from the pressure in a blood vessel. The invention is not, however, restricted to the structure of the heart rate equipment used. A relevant point to the invention is, however, that the heart rate monitor comprises means for transmitting heart rate information to an external computer or the like.

In a preferred embodiment of the invention, a number of classes is specified on the basis of which the user can be identified. Such physiological parameters include, for example, the user's weight, age, maximum oxygen uptake or some such variable. The user undergoes measurements in each physiological class, whereby the user can be classified by using the specified physiological classes. For example, the following combination of variables can be measured for a certain person: 83 kg −47–35 ml//kg/min. In the physiological class weight, the classification may be based on intervals of 5 kg, for example, the user thus belonging to weight range 80 to 85 kg. The invention comprises calculating several results, such as e.g. the mean heart rate, standard heart rate deviation, respiratory rhythm identifiable from the heart rate or other such variables describing the heart rate, from the heart rate information measured from the performer of a fitness exercise. The heart rate information results and the physiological variables described above are dependent on each other, and this fact is utilized in the invention. This can be exemplified by said weight class of 80 to 85 kg; the mean heart rate, standard heart rate deviation and respiratory rhythm identifiable on the basis of the heart rate can be specified for persons belonging to this class.

In a preferred embodiment of the invention, the dependence between the heart rate information results, i.e. the input parameters, and the classes, i.e. the output parameters, is modeled by utilizing a mathematical model. The mathematical model used can be, for example, a neural network which is taught to draw conclusions on the effect of each input parameter on each output parameter by using sufficiently large user data. In a preferred embodiment of the invention, when heart rate information data has been fed to the model and certain output parameter values obtained as the output, it is highly probable that the user will be identified.

In a preferred embodiment of the invention, the execution date and time of an exercise are stored in connection with the exercise and they are encrypted such that the user cannot affect or change them. This enables the possibility to be eliminated that the heart rate information stored by the user on the exercise were copied and used on several different days, for example.

An advantage of the invention is that a performer of an exercise can be identified in a more reliable manner compared with the known methods.

BRIEF DESCRIPTION OF THE DRAWINGS

In the following, the invention will be described in closer detail with reference to the accompanying drawings, in which.

DETAILED DESCRIPTION OF EMBODIMENTS

Figure 1A:
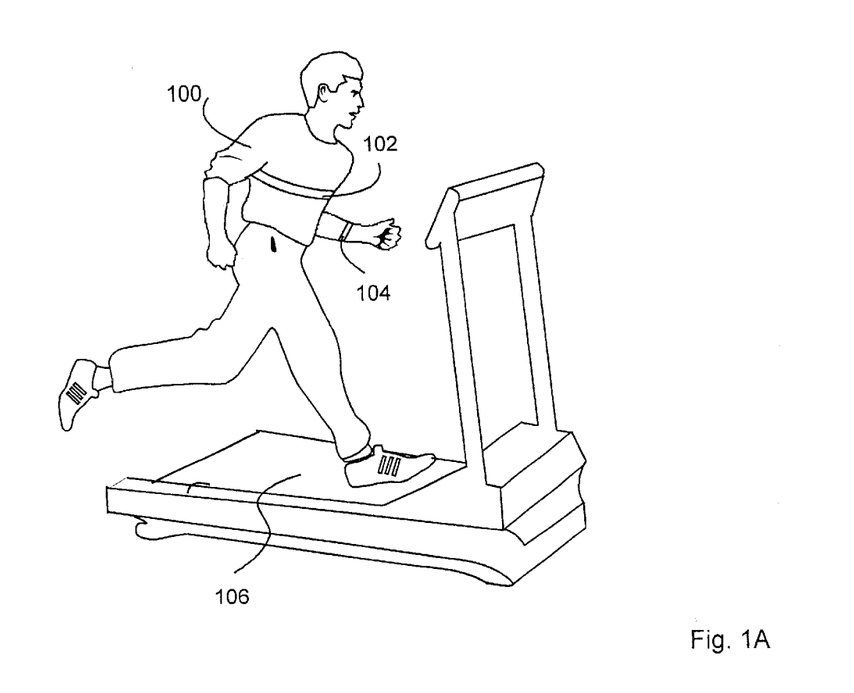
FIG. 1A shows a person performing a running exercise on a treadmill, the heart rate of the performer being measured by a heart rate monitor.

In the following, the invention will be described by means of the preferred embodiments and with reference to the accompanying drawings 1A to 5B. FIG. 1 shows a person 100 performing an exercise on a treadmill 106. The heart rate of the person 100 is measured by a transmitter electrode belt 102 arranged on the chest. The heart rate is measured by two or more electrodes 110A and 110B in the transmitter electrode belt 102, a potential difference being formed between the electrodes when the heart beats. The transmitter electrode belt 102 is attached around the person's body by using, for example, an elastic band made of an elastic material. The measured heart rate is preferably inductively transmitted to a receiver 104 on the wrist, which preferably also comprises a display for showing the measured heart rate. The invention is also suitable for heart rate monitors in which an electrode belt 102 on the chest is responsible for, in addition to measuring the heart rate, storing, processing and displaying the heart rate information, in which case no separate receiver 104 arranged on the wrist is needed. The heart rate monitor may also be a mere wrist device wherein the transmitter part and the receiver part are integrated into one device, in which case no transmitter and receiver electronics are needed. The heart rate can be measured on the wrist either from an EKG signal describing the arterial pressure pulse or by optically detecting changes in absorption or reflection in the blood flow.

Figure 1B:
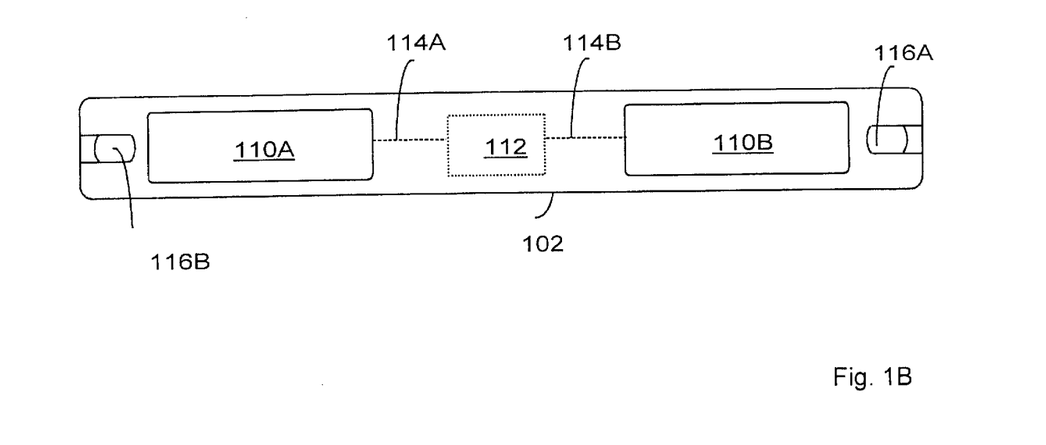
FIG. 1B shows an electrode belt shown in FIG. 1 as seen from the side to be arranged against the person's body to be measured.

FIG. 1B shows the electrode belt 102 shown in FIG. 1A in greater detail. In FIG. 1B, the electrode belt 102 is described as seen from the side of the electrodes 110A and 110B, i.e. the side to be arranged against the body. The figure further shows fasteners 116A and 116B, by which the electrode belt 102 can be fastened to the elastic band attached around the body. The fasteners 116A and 116B are preferably nest-like slots in the electrode belt 102 to receive button parts in the elastic band. Using a broken line, FIG. 1B further shows an electronics unit 112 for processing the heart rate information received from the electrodes 110A and 110B. The electrodes 110A and 110B are connected to the electronics unit 112 by conductors 114A and 114B respectively.

Figure 1C:
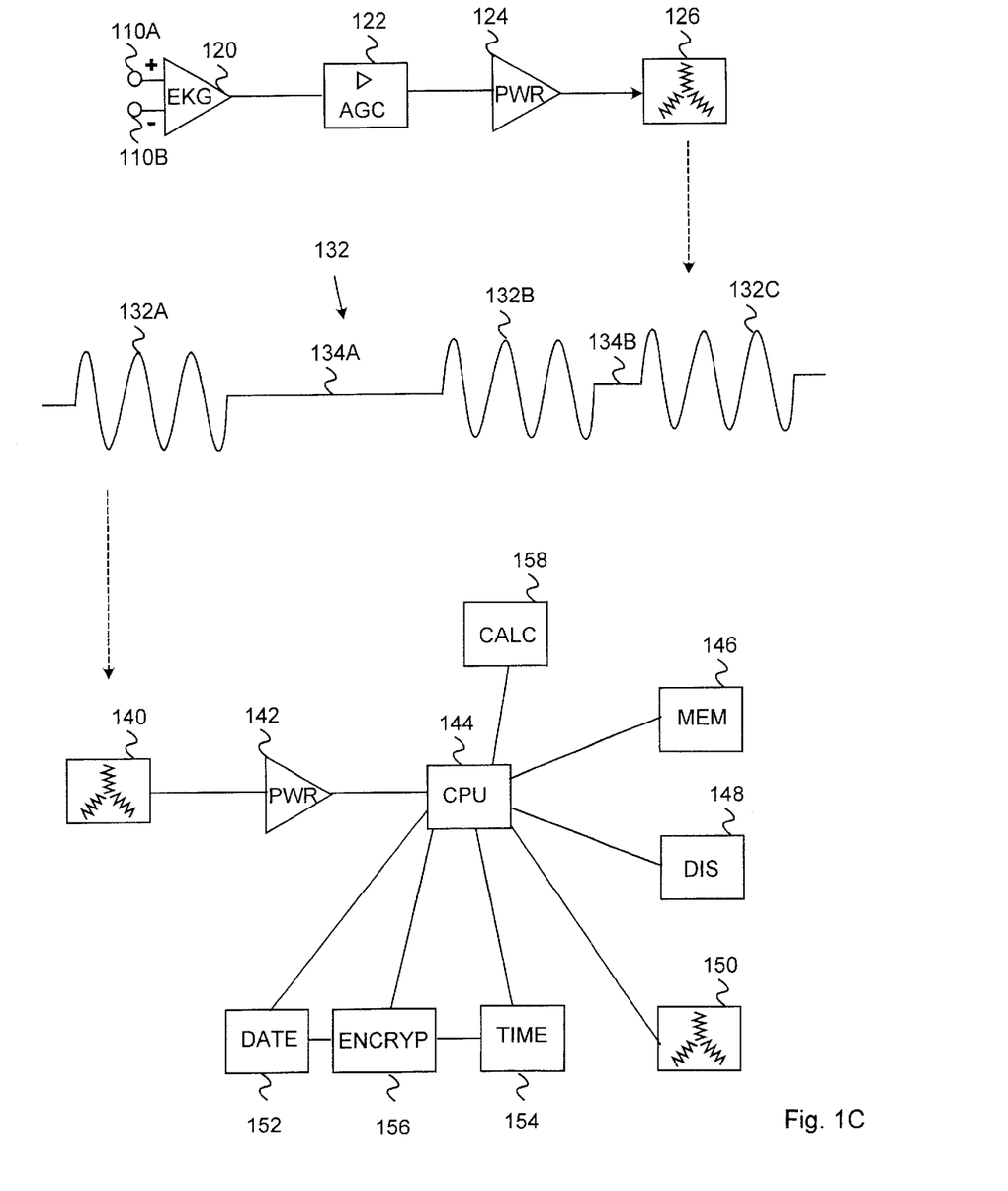
FIG. 1C is a block diagram showing an embodiment of a two-piece heart rate monitor, FIG. 2A roughly shows the structure of a mathematical model according to an embodiment of a method of the invention.

FIG. 1C shows structures of the transmitter electrode belt 102 and the receiver 104 by means of an embodiment. The transmitter electrode belt 102 is shown at the top of the figure, a sample of the heart rate information to be transmitted in the middle, and the relevant parts of the receiver unit 104 at the bottom. The electrode unit 112 of the transmitter electrode belt 102 receives the heart rate information from means for measuring one or more parameters 110A and 110B of the heart rate information. The measuring means are preferably electrodes, and the heart rate monitor comprises at least two, but possibly also more, such electrodes. From the electrodes, the signal progresses to an EKG preamplifier 120 from which the signal is transmitted to a transmitter 126 through an AGC amplifier 122 and a power amplifier 124. The transmitter 126 is preferably implemented as a coil which inductively transmits heart rate information 130 to a receiver, such as the receiver unit 104 arranged on the wrist or, for example, an external computer.

One beat of the heart corresponds with one 5 kHz burst 132A, for example, or one beat may correspond to a group 132A to 132C comprising several bursts. The intervals 132A and 132B between the bursts 130A to 130C may be equal in length or they may differ in length, such a situation being shown in FIG. 1C. Information may be transmitted inductively or, alternatively, optically or through a conductor, for example. In an embodiment, the receiver 104, such as the receiver arranged on the wrist, comprises a receiver coil 140 from which the received signal is, through a signal receiver 142, supplied to a central processing unit 144 coordinating the operation of the different parts of the receiver 104. The receiver 104 preferably also comprises a memory 146 for storing the heart rate information and a display 148 for showing the pulse or pulse variables derived therefrom, such as the standard deviation. In a preferred embodiment, the receiver 104 also comprises means 150 for transmitting the heart rate information to, for example, an external computer or an information network, such as the Internet. The transmitting means 150 may be implemented as an inductive coil, optical transmitter or by a connector for transmission through a connecting line, for example. A mathematical model 158, which will be described in closer detail in connection with FIGS. 2 and 4, may also be implemented in the receiver 104. In such a case, the transmitter 150 transmits the user identifier values formed in one or more classes by the mathematical formula 158.

In a preferred embodiment, by using means for forming a date 152 of a fitness exercise in connection with the fitness exercise, the execution date of the exercise is coded into the heart rate information before it is transmitted to the transmitter 150. The heart rate monitor also comprises means for adding the formed date to the heart rate information collected on the exercise in order to confirm the execution date of the fitness exercise. In an embodiment, the date is presented in form 151099, which means Oct. 15$^{th}$ 1999. By using means for forming an execution time 154 of a fitness exercise in connection with the fitness exercise, the execution time of the exercise may also be coded into the heart rate information. The heart rate monitor also comprises means for adding the formed execution time to the heart rate information collected on the fitness exercise in order to confirm the execution time of the fitness exercise. In an embodiment, the execution time of the exercise may be presented in form 183515, which means 18 hours 35 minutes and 15 seconds. The execution time of the exercise may also be replaced by the duration of the exercise. The execution time of the exercise may also be transmitted as information designating two different aspects of time, i.e. the starting time of the exercise and the ending time of the exercise. If the exercise is performed when the day changes, also the date is transmitted twice, i.e. at the outset and at the end of the exercise. The date may, of course, be transmitted two or more times also at other times than when the day changes. It is obvious that the invention is not restricted to the form in which the date and/or time is presented. Neither is the invention restricted to whether the date and/or time is transmitted one, two or possibly even more times. If the date or time is added to the heart rate information, it is preferably encrypted by means 156 for encrypting. The date and/or time information is preferably added to the heart rate information entirely unnoticed by the user, or if the information can be seen by the user, such that it cannot be changed by the user. In a preferred embodiment, the encryption module 156 operates for instance such that the date is encrypted by a first encryption algorithm and the time is encrypted by a second encryption algorithm. In a simple embodiment, the first encryption algorithm may, for example, mean that the date is multiplied by 5, and the second encryption that the time is divided by 3. The invention is not restricted to what said first and second encryption algorithms are like, i.e. how the date and/or time is encrypted. In connection with the invention, the time of the exercise, i.e. the execution time, refers to time information on the basis of which the execution time of the exercise can be confirmed. In a preferred embodiment, the starting time of the exercise (date and time) is added to the beginning of the fitness exercise information and the ending time to the end of the fitness exercise information. According to another preferred embodiment, the execution time refers to a combination of the starting time and duration of the exercise. In an embodiment, the heart rate monitor and particularly the receiver equipment 104 thereof also comprise a memory 146 for storing the heart rate information during the exercise so as to be, for example, transmitted to the computer only after the exercise and not real-time during the exercise. In a preferred embodiment, the means for forming the date 152, means for adding dates 152, means for forming the execution time 154, means for adding the execution time 154 and encryption means 156 are implemented by software on a central processing unit 144. The means may also be implemented as ASIC or by separate logic components.

In the embodiment according to FIG. 1C, the heart rate monitor refers to an integrated whole comprising the transmitter electrode belt 102 and the receiver 104. In a preferred embodiment, the heart rate monitor may also be implemented such that the above-described functions in the transmitter electrode belt 102 and the receiver 104 are located in one device. The one-piece device may either be one to be placed on the chest for the heart rate measurement or, alternatively, one to be used on the wrist. It is obvious to one skilled in the art that the electrode belt 102 and the receiver 104 may also comprise other parts than those shown in FIGS. 1B and 1C, but it is irrelevant to describe them herein.

Figure 2A:
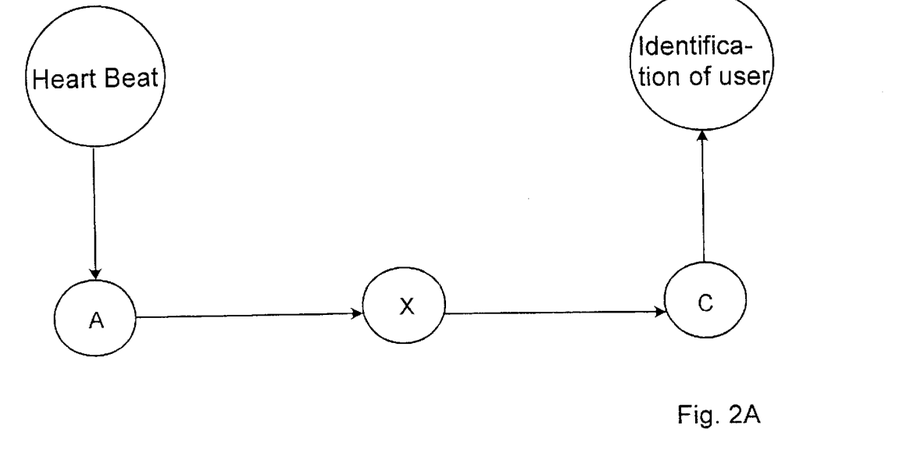
Figure 2B:
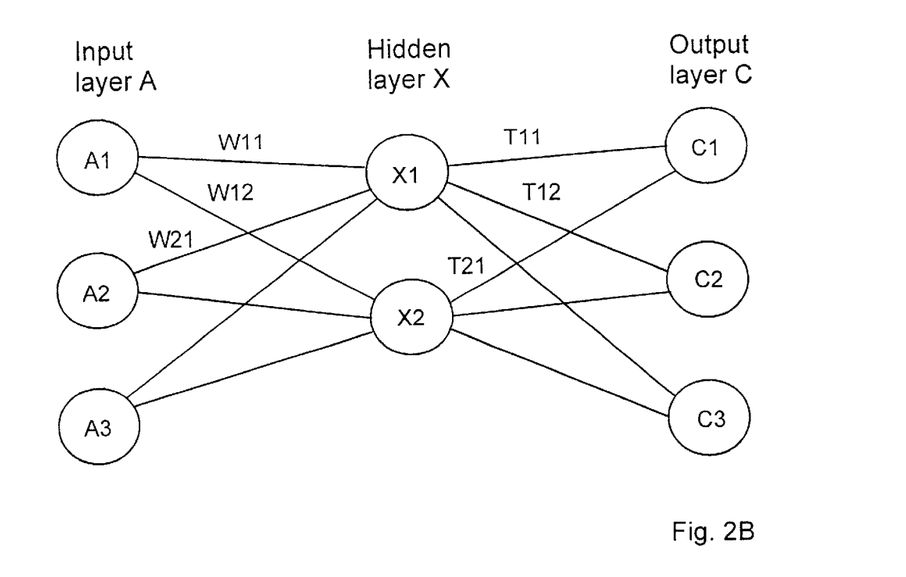
FIG. 2B shows the model shown in FIG. 2A in greater detail.

In FIGS. 2A and 2B, the operation of a mathematical model according to an embodiment of the invention is described in a rough manner. Referring to FIGS. 2A and 2B, the heart rate information is supplied to input layer A, the heart rate information being divided into elements A1 to A3 obtained from the heart rate information, such as the mean heart rate, standard heart rate deviation during the exercise or respiratory frequency calculated from the heart rate. The input layer elements are weighted by weighting coefficients W, the figure only showing a few W11 . . . W21 for the sake of clarity. W11 designates the weight of a first factor in the input layer for first factor X1 in hidden layer X, W12 designates the weight of first factor A1 of the input layer for second factor X2 in the hidden layer, etc. The value of hidden layer X1 thus depends on the sums of factors A weighted by weighting coefficients W. A further factor is constant summing term B. The dependence may be linear or non-linear, which is described by function F in formula (1). The hidden layer elements are weighted correspondingly by weighting coefficients T, which, as the output, gives factors C1 to C3 corresponding to the physiological classes of output layer C. The physiological elements of the output layer given as the output of the model may include, for example, the measured person's weight, height, age or physical condition measured by the maximal oxygen uptake, for example. According to the model, each input parameter is thus dependent on each output layer parameter. The mathematical model described above is called a neural network, and, adapted to FIG. 2B, C1, for example, it may be presented according to formula (1):

$$C_1 = T_{11}F_1(W_{11}A_1 + W_{21}A_2 + W_{31}A_3 + B1) + T_{21}F_2(W_{12}A_1 + W_{22}A_2 + W_{32}A_3 + B2) + B3 \quad (1)$$

wherein B1 to B3 describe the biasing vector, i.e. summation term, associated with each layer. For the sake of clarity, the biasing vector is not described in the figure.

As to the neural networks, it is to be noted that the model is preferably taught by a large group, such as information collected from hundreds of people, for example. Optimal values can thus be found for weighting coefficients W, sum factors B and function F shown in formula (1). Function F can be linear or non-linear, as a sigmoid function.

Figure 3:
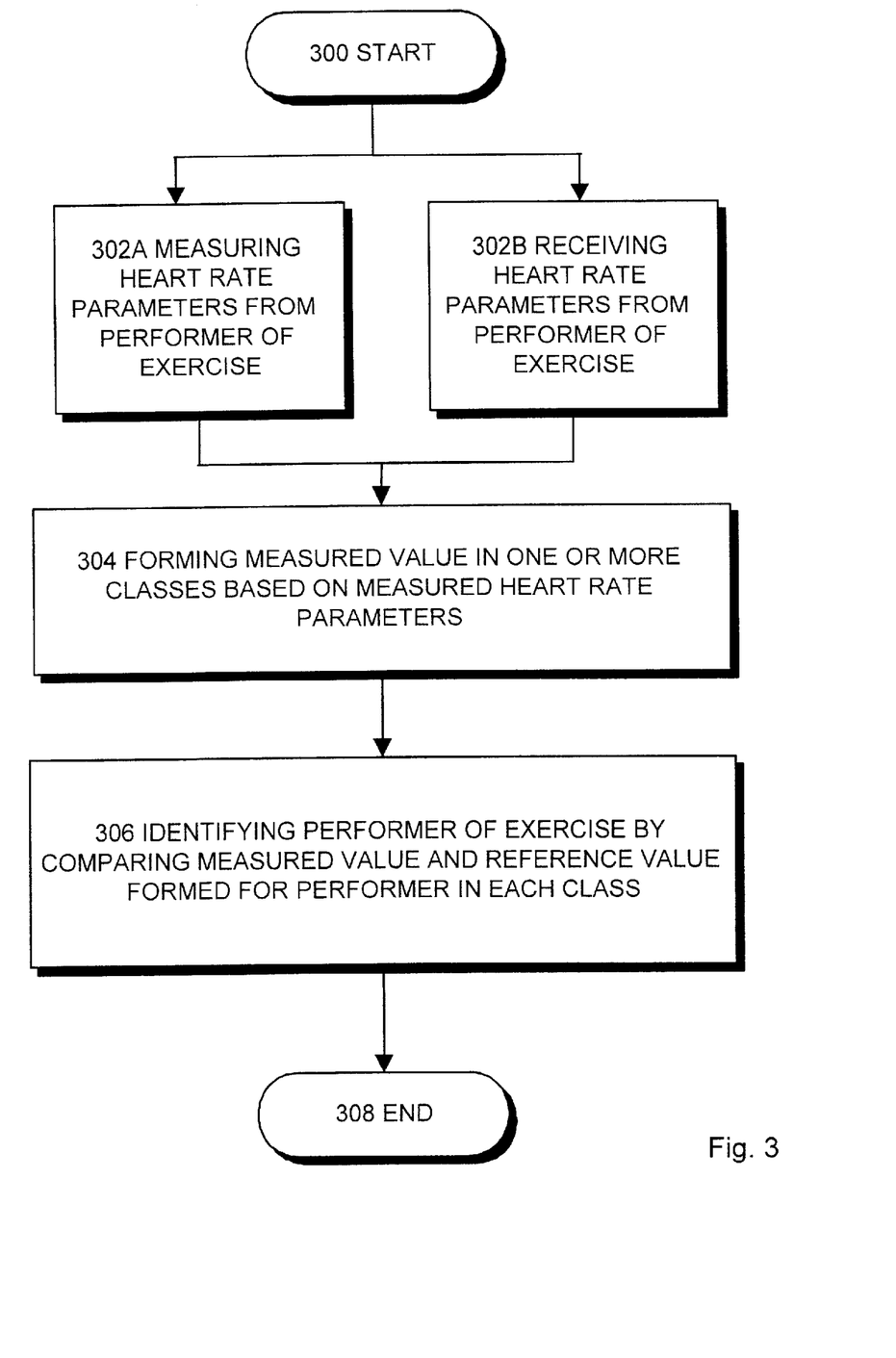
FIG. 3 is a method diagram showing an embodiment of the method of the invention.

An embodiment of the method of the invention is described in FIG. 3 in form of method steps. In starting step 300 of the method, a user has received a fitness program from his or her fitness instructor, and the user is expected to follow the program. The reference values of the user in different classes have been specified with the instructor, i.e. it has been established that the user is e.g. 45 years old and weighs 95 kg. The reference values can, of course, also be formed after the exercise has been performed when the instructor makes sure that it is precisely the desired user who has performed the exercises listed in the fitness program. Furthermore, in step 300, the user has set a heart rate monitor to measure his or her heart rate. The heart rate is measured in step 302A, and the measurement can be carried out during one or more of the following periods: before the exercise, during the exercise or after the exercise. By means of the mathematical model, a measuring value is formed 304 in one or more classes selected in advance. The preselected classes may be physiological classes, such as sex, weight, height or age. The classes may also be based on the heart rate information, such as the minimum heart rate, maximum heart rate, mean heart rate, standard heart rate deviation or spectral efficiency. The physiological classes and the classes based on the heart rate information are not mutually exclusive but the selected classes may comprise classes from both groups. The classes selected for identifying the user thus preferably comprise both physiological classes and classes based on the heart rate information, but this is not necessary. It can be generally noted, however, that the user identification is the more reliable the more classes used in the identification. In method step 306, the performer of the fitness exercise is identified by comparing the measured heart rate parameters with the reference values measured in different classes. One or more of the following may be used as the heart rate parameters: the minimum heart rate, maximum heart rate, mean heart rate or spectral efficiency. The user can be identified on the basis of the obtained data in many ways; for example, the instructor may approximately estimate how well the measured values conform with the reference values of the performer of the fitness exercise formed in different classes. This method is not, however, suitable for situations wherein the instructor has many trainees to watch. The estimation process described above can be specified by, for example, forming a 10% margin of error around the measurement value and checking whether the measurement values fit in the ranges determined for the reference values., Furthermore, it may well be that as regards one heart rate parameter, the heart rate information measured from the user does not correlate with that measured from persons of similar age and weight, for example. When it is estimated whether or not a certain person has performed the desired exercises, the misleading value of the heart rate parameter mentioned above can, for example, then be ignored. In a preferred embodiment, the user is identified by software, using a separate identification device which receives the identifier values formed for the user and the reference values in different classes as the input information and returns the user identifier as the output. Method steps 300, 302B, 304, 306, 308 describe the situation from the point of view of a computer product. The heart rate is then measured by the heart rate monitor and, as seen from the point of view of the computer product, the method steps are initiated with a step wherein the heart rate has been measured earlier and it is necessary only to receive the heart rate information.

Figure 4:
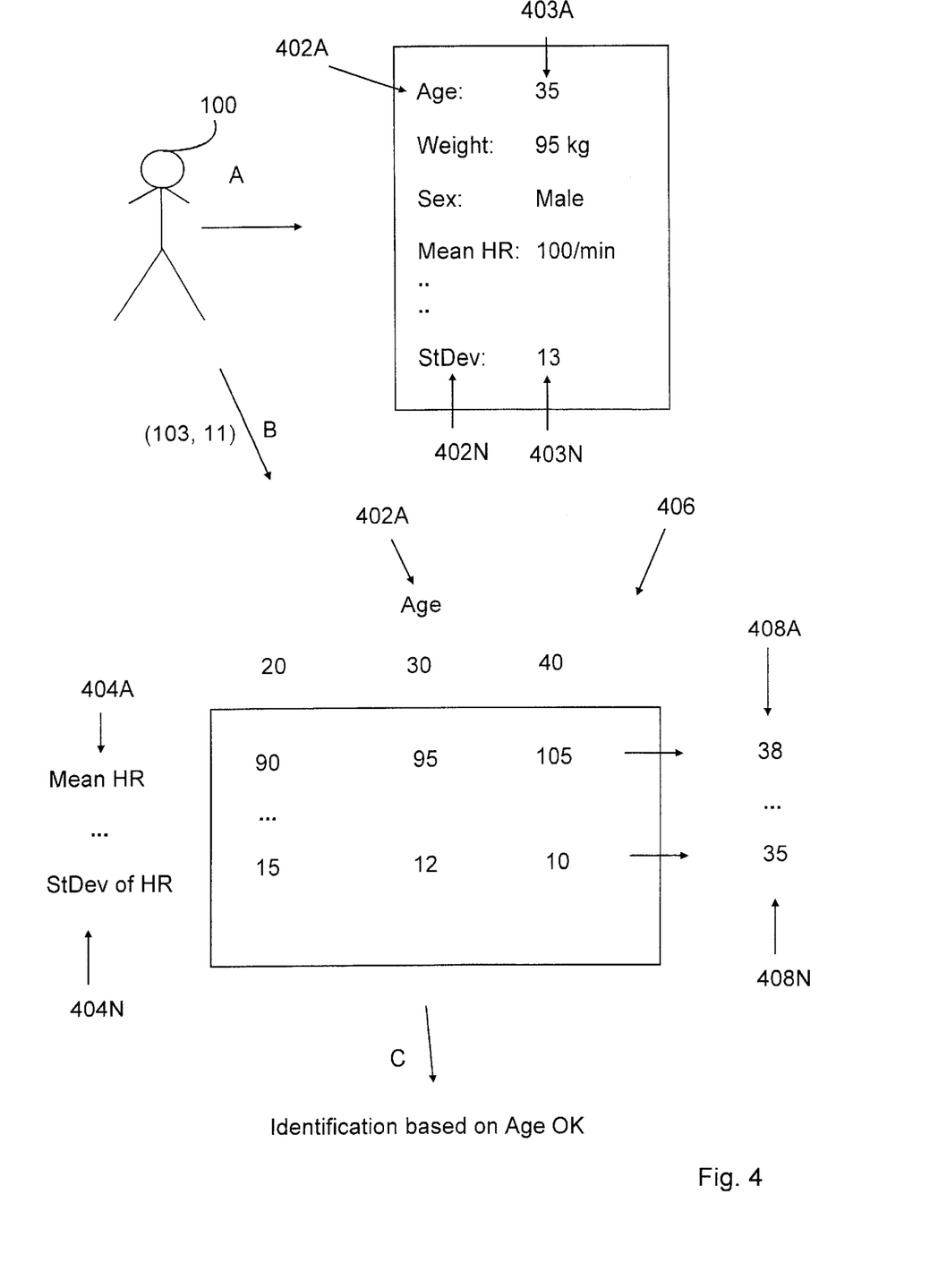
FIG. 4 shows an example of the method of the invention.

The method of the invention described in FIG. 3 will be described next by utilizing an example shown in FIG. 4. The person 100 shown in FIG. 4 is the target to be measured, i.e. the person whose execution of a fitness exercise is monitored. The figure shows phase A, which designates that the person 100 is measured for reference values in each class 402A to 402N, which may be physiological classes or classes comprising heart rate parameters. Classes 402A to 402N are shown inside a box, i.e. in the example of FIG. 4 there are five classes 402A to 402N: age, weight, sex, mean heart rate during a particular exercise and standard heart rate deviation during the same particular exercise. The invention is not restricted to how many classes 402A to 402N are used. In phase B, the person 100 performs the exercise assigned by his or her instructor, and during the exercise the heart rate monitor stores, either in itself or in a computer connected thereto, values (103, 11) shown in brackets, 103 designating the heart rate during the exercise and 11 designating the standard heart rate deviation during the exercise. The figure comprises two heart rate parameters 402A to 402N, mean heart rate 404A and standard heart rate deviation 404N, but naturally there may be more or less than two parameters. Part of the mathematical model 406 is described in a simplified manner as regards the fact that the model 406 discloses the value given by the model 406 corresponding to each heart rate information parameter in class 402A age. Hence, for example, the mean heart rate (90) during the exercise corresponds with a value (20) years in class 402A age. Returning to the example, the mean heart rate of the person 100 during the exercise was 103, which gives an estimated age 38. The standard heart rate deviation of the person 100 was 11, which gives an estimated age 35. FIG. 4 describes the mathematical model 406 only as regards one class 402A, i.e. class age, but a corresponding model 406 is formed also for the rest of the classes.

The equipment according to a preferred embodiment of the invention will be described next with reference to FIGS. 5A and 5B. FIG. 5 shows a receiver 104 of the heart rate monitor to be arranged on the wrist, the operation of the receiver being described in connection with FIG. 1C as regards relevant parts to the invention. The invention is not restricted to the fact that the heart rate monitor comprises a receiver unit to be arranged on the wrist, but the heart rate monitor in its entirety may be located in an electrode belt to be arranged on the chest, in which case the functions shown in FIG. 1C are located in the electrode belt. In a preferred embodiment, the heart rate information measured by the heart rate monitor is transferred to a-separate identifier device 500, which, in a preferred embodiment, is a separate computer for identifying a person. According to another embodiment, all equipment and information necessary for identifying the performer of a fitness exercise are located in the electrode belt 102 itself or in the receiver unit 104. The computer 500 preferably comprises a display 502 for showing the procedures carried out by the computer 500. The computer 500 further comprises a central processing unit 504 whose structure will be described in closer detail in FIG. 5B. Returning to FIG. 5A, the computer comprises means 506 for supplying information to the computer, such as a keyboard or a mouse,for example. Furthermore, the computer 500 comprises means 508 for receiving the heart rate information from a heart rate monitor 104. In a preferred embodiment, the receiving means 508 are, for example, a telecommunication port of the computer 500 to which the heart rate monitor can be connected through a cable. The receiving means 508 may also be implemented as an inductive coil or an optical reader. The receiving means 508 can thus be compared to the receiver of the heart rate monitor shown in FIG. 1C, i.e. substantially comprising parts 140 and 142.

Figure 5A:
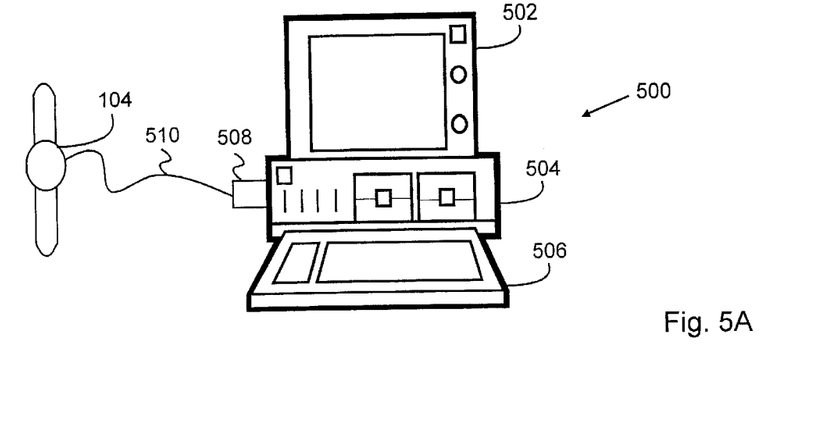
FIG. 5A shows an arrangement of an embodiment of the invention for identifying a person.

A preferred arrangement for measuring heart rate information shown in FIG. 5A comprises the heart rate monitor and the computer connected thereto. It is possible, however, that the shown equipment is located in a place where the performer of the exercise performs the exercise while the instructor of the exercise is located in a different physical place where he or she has a separate computer. The computer 500 of the performer of the exercise and the instructor's computer may communicate utilizing the prior art methods, for example through the Internet, e-mail or the like.

Figure 5B:
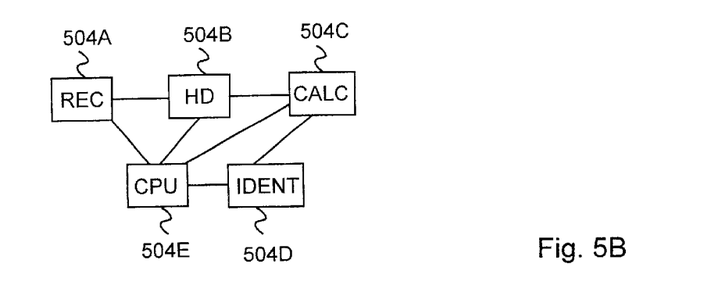
FIG. 5B shows the block structure of a computer according to an embodiment of the invention.

The structure of the central processing unit 504 of the computer is described in FIG. 5B as regards relevant parts to the invention. The central processing unit 504 shown in FIG. 5B comprises receiving means 504A for receiving the heart rate information received from the heart rate monitor from the serial port 508 or the like. The central processing unit preferably also comprises memory means 504B, such as a hard disk, for storing the heart rate information. In a preferred embodiment, the mathematical model of the invention and the data necessary for the model are stored on the hard disk of the computer, but it is also possible to store them on a diskette, CD-ROM or other such memory means 504B. The computer comprises means for classifying the performer of the exercise in one or more classes. The computer also comprises calculating means 504C for forming, on the basis of the measured heart rate information parameters, an identifier value in one or more classes by means of a mathematical model comprising dependence information between the heart rate information parameters and the classes. The computer 500 also comprises means 504D for comparing the identifier values formed for the performer of the exercise with the reference values. The computer 500 also comprises means 504D for concluding the performer of the fitness exercise on the basis of comparisons between the identifier values and the reference values. The comparing and concluding processes can be carried out in many different ways; hence, the means 504D for comparing and concluding can also be implemented in different ways. Stored on the hard disk 504B, the classifying means, the calculating means 504C, comparing means 504D and concluding means 504D are preferably implemented by software, but they may also be implemented as ASIC or by separate logic components. Logically, the operation of the confirming means 504D can be thought such that, for example, the classes are arranged in order of competence, which means that the person is identified with respect to the most representing class. In such as case, for example, it is feasible that the dependence between the heart rate information parameters and the sex of the person to be measured is obtained from the mathematical model at a probability of 95%. The second best criterion might be weight, for example, in which case next the weight of the person would be determined on the basis of the dependence between the heart rate information parameters and weight. The process continues until the person is identified. The present invention is not restricted to what the method used for identifying the person on the basis of the identifier values formed in the classes is. The operation of the computer is controlled by a processor 504E, which, according to the prior art, is responsible for processing the commands supplied from the supplying means 506 and showing the outlet of the programs stored on the computer by the display means 502. The lines shown in the figure between the different parts describe by way of example the connections between the parts: hence, for example, the parts 504B and 504E are connected, i.e. the processor and the software logic therein control the operation of the memory means 504B. It is obvious that the central processing unit also comprises other parts and connections therebetween, but it is irrelevant to describe the operation of those parts in this connection.

Although the invention has been described above with reference to the examples according to the accompanying drawings, it is obvious that the invention is not restricted thereto but can be modified in many ways within the inventive idea disclosed in the attached claims.

What is claimed is:

1. A method of confirming a performer of a fitness exercise, the method comprising the following steps:

measuring heart rate information associated with the performer of the fitness exercise as regards the fitness exercise;

forming an identifier value in one or more classes on the basis of one or more parameters of the measured heart rate information by means of a mathematical model comprising dependence information between said parameter of the heart rate information and said class;

confirming the performer of the fitness exercise by comparing in said one or more classes the identifier value with a reference value formed for the performer of the fitness exercise in the class.

2. A method as claimed in claim 1, further comprising the steps of:
  forming an execution date of the fitness exercise in connection with the fitness exercise;
  adding said date to the heart rate information collected on the fitness exercise in order to confirm the execution date of the fitness exercise.

3. A method as claimed in claim 2, further comprising the step of:
  encrypting the execution date of the fitness exercise by a first encryption algorithm.

4. A method as claimed in claim 1, further comprising the steps of:
  forming an execution time of the fitness exercise in connection with the fitness exercise;
  adding said execution time to the heart rate information collected on the fitness exercise in order to confirm the execution time of the fitness exercise.

5. A method as claimed in claim 4, further comprising the step of:
  encrypting the execution time of the fitness exercise by an encryption algorithm.

6. A method as claimed in claim 1, wherein said mathematical model is a neural network, the mathematical model having been taught by a sufficiently large amount of real measurement results concerning the effects of the user heart rate information in different classes.

7. A method as claimed in claim 1, wherein said class used is one or more of the following physiological classes: age, sex, height or weight.

8. A method as claimed in claim 1, wherein said class used is one or more of the following classes describing the heart rate: minimum heart rate, maximum heart rate, mean heart rate, standard heart rate deviation or spectral efficiency.

9. A method as claimed in claim 1, wherein the heart rate information parameter used is one or more of the following parameters: minimum heart rate, maximum heart rate, mean heart rate, standard heart rate deviation or spectral efficiency.

10. An arrangement for confirming a performer of a fitness exercise, the arrangement comprising:
  a heart rate monitor for measuring one or more parameters of heart rate information associated with the performer of the fitness exercise as regards the fitness exercise;
  identifier equipment comprising:
    means for classifying the performer of the fitness exercise in one or more classes;
    a mathematical model comprising dependence information between said one or more parameters of the heart rate information and said one or more classes;
    and calculating means for forming an identifier value in one or more classes on the basis of one or more parameters of the heart rate information by means of the mathematical model;
    means for comparing in said one or more classes the identifier value of the performer of the fitness exercise with a reference value formed for the performer of the fitness exercise in the class;
    means for concluding the performer of the fitness exercise on the basis of the comparison between the identifier values and the reference values.

11. An arrangement as claimed in claim 10, wherein the heart rate monitor comprises means for transmitting the heart rate information wirelessly or through a connecting line from the heart rate monitor to the calculating means.

12. An arrangement as claimed in claim 10, wherein the identifier equipment comprises means for receiving the heart rate information transmitted wirelessly or through the connecting line from the heart rate monitor.

13. An arrangement as claimed in claim 10, wherein the heart rate monitor comprises means for forming an execution date of the fitness exercise in connection with the fitness exercise and adding said date to the heart rate information collected on the fitness exercise in order to confirm the execution date of the fitness exercise.

14. An arrangement as claimed in claim 13, wherein the heart rate monitor comprises means for encrypting the execution date of the fitness exercise by a first encryption algorithm.

15. An arrangement as claimed in claim 10, wherein the heart rate monitor comprises means for forming an execution time of the fitness exercise in connection with the fitness exercise and adding said execution time to the heart rate information collected on the fitness exercise in order to confirm the execution time of the fitness exercise.

16. An arrangement as claimed in claim 15, wherein the heart rate monitor comprises means for encrypting the execution time of the fitness exercise by a second encryption algorithm.

17. An arrangement as claimed in claim 10, wherein said mathematical model is a neural network, the mathematical model having been taught by a sufficiently large amount of real measurement results concerning the effects of the user heart rate information in different classes.

18. An arrangement as claimed in claim 10, wherein said class used is one or more of the following physiological classes: age, sex, height or weight.

19. An arrangement as claimed in claim 10, wherein said class used is one or more of the following classes describing the heart rate: minimum heart rate, maximum heart rate, mean heart rate, standard heart rate deviation or spectral efficiency.

20. An arrangement as claimed in claim 10, wherein the heart rate information parameter used is one or more of the following parameters: minimum heart rate, maximum heart rate, mean heart rate, standard heart rate deviation or spectral efficiency.

21. A computer software product for confirming a performer of a fitness exercise, the product comprising a program stored in a device for storing programs and readable by a computer, and the program being arranged to perform the following method steps:
  receiving heart rate information associated with the performer of the fitness exercise as regards the fitness exercise;
  forming an identifier value on the basis of parameters of the measured heart rate information in one or more classes by means of a mathematical model comprising dependence information between the parameters of the heart rate information and the classes;
  confirming the performer of the fitness exercise by comparing in said one or more classes the identifier value with a reference value formed for the performer of the fitness exercise in the class.

22. A computer software product as claimed in claim 21, wherein said mathematical model is a neural network, the mathematical model having been taught by a sufficiently large amount of real measurement results concerning the effects of the user heart rate information in different classes.

23. A computer software product as claimed in claim 21, wherein said class used is one or more of the following physiological classes: age, sex, height or weight.

24. A computer software product as claimed in claim 21, wherein said class used is one or more of the following classes describing the heart rate: minimum heart rate, maximum heart rate, mean heart rate, standard heart rate deviation or spectral efficiency.

25. A computer for confirming a performer of a fitness exercise, the computer comprising:

means for receiving one or more parameters of heart rate information associated with the performer of the fitness exercise as regards the fitness exercise;

means for classifying the performer of the fitness exercise in one or more classes;

a mathematical model comprising dependence information between said one or more parameters of the heart rate information and said one or more classes;

calculating means for forming an identifier value in one or more classes on the basis of one or more parameters of the heart rate information by means of the mathematical model;

means for comparing in said one or more classes the identifier value of the performer of the fitness exercise with a reference value formed for the performer of the fitness exercise in the class;

means for concluding the performer of the fitness exercise on the basis of the comparison between the identifier values and the reference values.

26. A computer as claimed in claim 25, wherein said mathematical model is a neural network, the mathematical model having been taught by a sufficiently large amount of real measurement results concerning the effects of the user heart rate information in different classes.

27. A computer claimed in claim 25, wherein said class used is one or more of the following physiological classes: age, sex, height or weight.

28. A computer as claimed in claim 25, wherein said class used is one or more of the following classes describing the heart rate: minimum heart rate, maximum heart rate, mean heart rate, standard heart rate deviation or spectral efficiency.

29. A computer claimed in claim 25, wherein the heart rate information parameter used is one or more of the following parameters: minimum heart rate, maximum heart rate, mean heart rate, standard heart rate deviation or spectral efficiency.

30. A method as claimed in claim 2, further comprising the steps of:

forming an execution time of the fitness exercise in connection with the fitness exercise;

adding said execution time to the heart rate information collected on the fitness exercise in order to confirm the execution time of the fitness exercise.

31. An arrangement as claimed in claim 13, wherein the heart rate monitor comprises means for forming an execution time of the fitness exercise in connection with the fitness exercise and adding said execution time to the heart rate information collected on the fitness exercise in order to confirm the execution time of the fitness exercise.

* * * * *

UNITED STATES PATENT AND TRADEMARK OFFICE
CERTIFICATE OF CORRECTION

PATENT NO.   : 6,428,476 B1
DATED        : August 6, 2002
INVENTOR(S)  : Heikkila et al.

It is certified that error appears in the above-identified patent and that said Letters Patent is hereby corrected as shown below:

Column 3,
Line 4, now reads " in the. dependent claims." should read -- in the dependent claims. --;

Column 5,
Line 7, now reads "Using a broken line," should read -- Using a broken line, Figure 1B --;

Column 7,
Line 33, now reads "$W_{32}A_{32}A_3+B2$" should read -- $W_{32}A_3+B2$ --; and Column 8,
Line 22, now reads "reference values., Furthermore" should read -- reference values. Furthermore --.

Signed and Sealed this

Thirty-first Day of December, 2002

JAMES E. ROGAN
*Director of the United States Patent and Trademark Office*